US010216064B2

(12) United States Patent
Mainz et al.

(10) Patent No.: US 10,216,064 B2
(45) Date of Patent: Feb. 26, 2019

(54) OPTICAL PARAMETRIC WAVEFORM SYNTHESIZER AND METHOD FOR SYNTHESIZING OPTICAL WAVEFORMS

(71) Applicant: Deutsches Elektronen-Synchrotron DESY, Hamburg (DE)

(72) Inventors: Roland Mainz, Hamburg (DE); Giulio Maria Rossi, Hamburg (DE); Franz Xaver Kaertner, Hamburg (DE); Oliver D. Muecke, Hamburg (DE); Giovanni Cirmi, Hamburg (DE)

(73) Assignee: Deutsches Elektronen-Synchrotron DESY, Hamburg (DE)

( * ) Notice: Subject to any disclaimer, the term of this patent is extended or adjusted under 35 U.S.C. 154(b) by 0 days.

(21) Appl. No.: 15/653,957

(22) Filed: Jul. 19, 2017

(65) Prior Publication Data

US 2018/0024415 A1 Jan. 25, 2018

(30) Foreign Application Priority Data

Jul. 20, 2016 (EP) .................................... 16001600

(51) Int. Cl.
| | |
|---|---|
| G02F 1/39 | (2006.01) |
| H01S 3/00 | (2006.01) |
| H01S 3/13 | (2006.01) |
| G01J 3/453 | (2006.01) |
| G01N 21/31 | (2006.01) |

(Continued)

(52) U.S. Cl.
CPC ................ *G02F 1/39* (2013.01); *G01J 3/453* (2013.01); *G01N 21/31* (2013.01); *G01N 21/41* (2013.01); *G02F 1/395* (2013.01); *H01S 3/0057* (2013.01); *H01S 3/1307* (2013.01);
(Continued)

(58) Field of Classification Search
CPC ....................................................... G02F 1/39
See application file for complete search history.

(56) References Cited

U.S. PATENT DOCUMENTS

| | | | |
|---|---|---|---|
| 8,390,921 B2* | 3/2013 | Kaertner | G02F 1/39 |
| | | | 359/330 |
| 9,019,507 B2* | 4/2015 | Kimura | G01J 3/45 |
| | | | 356/451 |

(Continued)

FOREIGN PATENT DOCUMENTS

EP    1724634 A1    11/2006

OTHER PUBLICATIONS

Cundiff et al. (2001). Optical frequency synthesis based on mode-locked lasers. Review of Scientific Instruments, 72(10), 3749-3771.

(Continued)

*Primary Examiner* — Rhonda S Peace
(74) *Attorney, Agent, or Firm* — Caesar Rivise, PC

(57) ABSTRACT

Parametric optical waveform synthesizer (100) creating optical waveforms (4) includes: pump source device (10); seed source device (20); optical parametric amplifier device (30) having master channel (30A) with at least one optical parametric amplifier unit (31A, 32A), and having at least one slave channel (30B, 30C), with at least one optical parametric amplifier unit (31B, 32B, 31C, 32C); beam combiner device (40), detector devices (50), and control system (60), which is configured for orthogonal control of seed source device (20) and optical parametric amplifier device (30).

18 Claims, 2 Drawing Sheets

(51) Int. Cl.
*G01N 21/41* (2006.01)
*H01S 3/23* (2006.01)

(52) U.S. Cl.
CPC ...... *G02F 2001/392* (2013.01); *H01S 3/0092* (2013.01); *H01S 3/2383* (2013.01)

(56) References Cited

U.S. PATENT DOCUMENTS

| | | | | |
|---|---|---|---|---|
| 9,057,930 | B2* | 6/2015 | Deng | G02F 1/39 |
| 9,912,852 | B2* | 3/2018 | Xu | H04N 5/2256 |
| 2018/0024415 | A1* | 1/2018 | Mainz | G02F 1/39 |

OTHER PUBLICATIONS

Fattahi et al. (2014). Third-generation femtosecond technology. Optica, 1(1), 45-63.

Harth et al. (2012). Two-color pumped OPCPA system emitting spectra spanning 1.5 octaves from VIS to NIR. Optics express, 20(3), 3076-3081.

Holman et al. (2003). Orthogonal control of the frequency comb dynamics of a mode-locked laser diode. Optics letters, 28(23), 2405-2407.

Huang et al. (2011). High-energy pulse synthesis with sub-cycle waveform control for strong-field physics. Nature photonics, 5(8), 475-479.

Manzoni et al. (2012). Coherent synthesis of ultra-broadband optical parametric amplifiers. Optics letters, 37(11), 1880-1882.

Manzoni et al. (2015). Coherent pulse synthesis: towards sub-cycle optical waveforms. Laser & Photonics Reviews, 9(2), 129-171.

Muecke et al. (2015). Toward waveform nonlinear optics using multimillijoule sub-cycle waveform synthesizers. IEEE journal of selected topics in quantum electronics, 21(5), 1-12.

Numata et al. (2014). Fast-switching methane lidar transmitter based on a seeded optical parametric oscillator. Applied Physics B, 116(4), 959-966.

Schibli et al. (2003). Attosecond active synchronization of passively mode-locked lasers by balanced cross correlation. Optics Letters, 28(11), 947-949.

Wirth et al. (2011). Synthesized light transients. Science, 334(6053), 195-200.

Ye et al. (2001). Molecular Iodine Clock. Physical Review Letters, vol. 87, No. 27, pp. 270801-1-270801-4.

European Search Report from corresponding EP 16001600 dated Jan. 20, 2017.

* cited by examiner

OPTICAL PARAMETRIC WAVEFORM SYNTHESIZER AND METHOD FOR SYNTHESIZING OPTICAL WAVEFORMS

CROSS-REFERENCE TO RELATED APPLICATIONS

This application claims priority from, EP 16 001 600.2, filed Jul. 20, 2016, the contents of which application are incorporated herein by reference in their entireties for all purposes.

BACKGROUND OF THE INVENTION

The invention relates to an optical parametric waveform synthesizer being configured for creating synthesized optical waveforms and to a method for synthesizing optical waveforms. Applications of the invention are available in particular in high-energy short-pulse laser sources based on OP(CP)A technology, in particular in OP(CP)A based waveform synthesizers ("Third Generation Femtosecond Laser Sources").

In the present specification, reference is made to the following publications cited for illustrating prior art techniques.
[1] S.-W. Huang et al. in "Nat. Phot." (vol. 5, no. 8, 2011);
[2] C. Manzoni et al. in "Laser & Photonics Reviews" (vol. 9, no. 2, 2015);
[3] O. D. Muecke et al. in "IEEE JSTQE" (vol. 21, No. 5, 2015);
[4] T. R. Schibli et al. in "Optics Letters" (vol. 28, no. 11, pp. 947-949 (2003));
[5] J. Ye et al. in "Physical Review Letters" (vol. 87, no. 27, pp. 270801-1-270801-4 (2001));
[6] K. W. Holman et al. in "Optics Letters" (vol. 28, no. 23, pp. 2405-2407 (2003));
[7] S. T. Cundiff et al. in "Review of Scientific Instruments" (vol. 72, no. 10, pp. 3749-3770 (2001)); and
[8] K. Numata et al. in "Applied Physics B: Lasers and Optics" (vol. 116, no. 4, pp. 959-966, 2014).

The demand for ultrashort and ultra-broadband laserpulses is increasing. Optical parametric chirped-pulse amplification (OP(CP)A) is the most promising candidate for a scalable high-energy, high-average power ultrashort pulse source, allowing the creation of multi-octave spanning spectra with controlled phase behavior, energy in the mJ range and at high repetition rate. In particular, the OP(CP)A technique allows for transferring energy from laser pulses with durations ranging from tens of femtoseconds to picoseconds and even nanoseconds (pump pulses) into pulses sustaining ultrashort compressed durations of few femtoseconds signal pulses. OP(CP)A amplifier crystals experience only low thermal load and high-energy pump lasers are available (e.g. Yb:YAG, Yb:YLF, Nd:YAG).

Based on the OP(CP)A technique, optical waveforms can be synthesized, as described e.g. in [1], [2] and [3]. An optical parametric waveform synthesizer typically includes multiple OP(CP)A channels with different spectral characteristics, which are coherently combined for synthesizing pulses (optical waveforms) with a desired temporal shape and spectral content. The optical parametric waveform synthesizer requires a well synchronized overlap in time and phase of the pump and seed pulses in the OP(CP)A channels and of the output pulses of the OP(CP)A channels.

With more details, from a common pump laser source or different synchronized pump laser sources, a passively-CEP-stable white-light seed is generated, split into different spectral OP(CP)A channels and stretched to match the pulse duration of the pump source(s). Each channel includes a chain of OP(CP)A-stages to reach the desired energy level. After amplification the pulses are recombined, e.g., with dichroic beam splitters for creating the optical waveforms to be obtained. Another possibility is to make use of different white-light seeds each optimized for different spectral OP(CP)A channels, all ideally derived from a common CEP-stable pulse.

To be able to synthesize/shape the light-field of the optical waveforms one needs to stabilize and control the envelopes and phases of the pulse(s) between the outputs of the different OP(CP)A channels as well as the carrier-envelope phases (CEPs) of the pulses. Furthermore, the pump and seed pulses need to be synchronized at each OPA stage.

The CEP of the white-light source might be passively stabilized (by passive-CEP stabilization e.g. DFG via OPA) and/or actively stabilized by measuring the f-2f beating and using a feedback control onto an appropriate optical element (e.g., changing dispersion by increasing/decreasing of glass wedges insertion), in order to account for environmental changes. Each channel of the seed is offered to an OPA-stage while ensuring temporal overlap with the corresponding pump pulse. This overlap does not need to be actively synchronized if the passive timing drifts between pump and seed are negligible compared to the duration of the pulses.

The arrival time difference (envelope time delay) between the outputs of two OP(CP)A channels can be measured by an appropriate technique, e.g., RAM, balanced optical cross-correlator (BOC), see e.g., [4], and the measured arrival time difference can be used to feedback control a delay line on the beam path of the pump of the last OP(CP)A stage of one of the two OP(CP)A channels. This locks together the pulse envelopes of the output of two OP(CP)A channels.

The other critical temporal property, in order to achieve a shot-to-shot stable synthesis, is the phase between the carrier waves of the different OP(CP)A channels. These are mainly affected by the interferometric instability between the different OP(CP)A channels from the splitting of the common seed (or common driver of the seeds) to its recombination after amplification. The relative phase between the carrier waves can be measured by beating spectral components from two separate outputs (if necessary by extending the spectral range of one or both outputs by means of nonlinear effects). The observed fringes in the spectrum carry information about the relative phase between the two contributing channels. This might take place in a high-resolution and single-shot spectrometer with dedicated electronics (e.g. FPGA, DSP, CPU) to calculate and track the phase of the fringe pattern, which allows for low-latency control, in particular active stabilization.

Accordingly, controlling the optical parametric waveform synthesizer, in particular stabilizing CEP and controlling the envelopes and phases between the outputs of the different OP(CP)A channels requires multiple control loops. However, the control loops are inherently coupled and influence each other, as exemplified in the following.

In the optical parametric waveform synthesizer, first the spectral modulations can be observed in the spectral overlap regions between adjacent channels to retrieve the relative phase between the OP(CP)A channel outputs. If this quantity needs correction, this is performed by moving a delay stage on the seed or amplified seed beam path before the last amplifier stage of one of the channels. This action ensures to lock the relative phase between the channels. However this produces a small change in the arrival time of the OP(CP)A channel output at the synthesis point. Recognizing this drift and moving the pump at this subsequent OPA stage requires time and results in a shift in the CEP of the amplified pulse. This mutual influence of the control loops requires a long time to stabilize and maybe never reach stable operation because each control loop will partly counteract the side effects of the other to bring its quantity back to the set-point.

Accordingly, control of conventional parametric waveform synthesizers is challenging (see e.g., [2]). In particular, it includes actuators with long response time which limits the bandwidth for control and stabilization, resulting in substantial limitations in practical applications of parametric waveform synthesizers.

It is generally known that inherent mutual interactions in coupled control loops can be decoupled by orthogonalization of the control, wherein the control is performed in such a way, that the signals given to the actuators are correlated such that only one controlled quantity, e.g., timing or phase, is varied at a time. Orthogonalized control has been mentioned in [2], [5], [6] and [7] controlling optical frequency synthesis with a mode-locked laser. However, this scheme was restricted to synchronizing higher repetition rate laser sources for example by controlling a mirror of the mode-locked laser, and it cannot be applied in controlling optical parametric waveform synthesizers. It was assumed in [2] that high-speed fluctuations in carrier phase and pulse timing between spectral channels would be common mode. Accordingly, [2] even suggests, that a specific control of these properties in optical parametric waveform synthesizers would not be necessary.

Publication [8] disclosing fast-switching a methane lidar transmitter based on a seeded optical parametric oscillator represents technological background with regard to OPA applications. However, publication [8] does not refer to the control of mode-locked lasers or the application of femtosecond or picosecond pulses.

The objective of the invention is to provide an improved optical parametric waveform synthesizer and an improved method of synthesizing optical waveforms, being capable of avoiding disadvantages and limitations of conventional techniques. In particular, the optical parametric waveform synthesizer is to be capable of synthesizing optical waveforms with a complete control on phase and timing from each spectral channel, in order to achieve huge tunability of the waveform, together with improved stability at shortened control response time.

These objectives are solved with an optical parametric waveform synthesizer and a method for synthesizing optical waveforms of the invention.

BRIEF SUMMARY OF THE INVENTION

According to a first general aspect of the invention, the above objective is solved by an optical parametric waveform synthesizer for synthesizing optical waveforms (electric field transients in the optical domain), comprising a pump source device for creating at least one sequence of pump pulses, a seed source device for creating a sequence of master seed pulses and at least one sequence of slave seed pulses, an optical parametric amplifier device having a master channel and at least one slave channel, each with at least one optical parametric amplifier unit (OP(CP)A stage) and being configured for creating a sequence of master channel laser pulses and at least one sequence of slave channel laser pulses based on one of the at least one sequence of pump pulses, the master seed pulses and one of the at least one sequence of slave seed pulses, a beam combiner device for coherently combining the master channel laser pulses and the slave channel laser pulses, thus synthesizing the optical waveforms to be obtained, and detector devices for sensing pulse properties of the master seed pulses, the slave seed pulses, the master channel laser pulses and the slave channel laser pulses.

According to the invention, the optical parametric waveform synthesizer includes an control system (or: control system device, in particular active stabilization device) for controlling in particular the CEP of the master and slave seed pulses and the relative temporal and relative phase relationships between the master channel laser pulses and the slave channel laser pulses on the basis of output signals of the detector devices, wherein the control system is configured for an orthogonal control of the seed source device and the optical parametric amplifier device. In particular, both of the relative temporal relationship and the relative phase relationship between the master channel laser pulses and the slave channel laser pulses are individually (separately) controlled by the control system.

Actuator devices of the seed source device and the optical parametric amplifier device generally comprise any components being configured for changing a temporal (envelope) and/or phase property of the laser pulses. Preferably, the actuator device in the seed source device comprise a dispersion setting device and/or a delay line between a pump and seed in a passively CEP stabilized OPA device. Furthermore, the actuator devices in the optical parametric amplifier device preferably comprise delay lines driven with piezoelectric drivers being arranged for locally adjusting the optical length in the seed/amplified seed or in the pump beam path of the optical parametric device or the pump beams.

According to a second general aspect of the invention, the above objective is solved by the method of synthesizing optical waveforms, comprising the steps of creating at least one sequence of pump pulses, creating a sequence of master seed pulses and at least one sequence of slave seed pulses, creating a sequence of master channel laser pulses by non-linear optical interactions using one of the at least one sequence of pump pulses and the master seed pulses in a master channel with at least one optical parametric amplifier unit and creating at least one sequence of slave channel laser pulses by non-linear optical interactions using one of the at least one sequence of pump pulses and the slave seed pulses in at least one slave channel with at least one optical parametric amplifier unit, wherein each of the sequence of master channel laser pulses and the at least one sequence of slave channel laser pulses has a specific spectral intensity characteristic, and coherently combining the master channel laser pulses and the slave channel laser pulses with a beam combiner device, thus synthesizing the optical waveforms to be obtained, wherein pulse properties of the master seed pulses, the slave seed pulses, the master channel laser pulses and the slave channel laser pulses are sensed.

According to the invention, the relative temporal and relative phase relationships between the master channel laser pulses and the slave channel laser pulses are orthogonally controlled on the basis of the sensed pulse properties. In particular, creating the sequence of master seed pulses, the at least one sequence of slave seed pulses, the sequence of master channel laser pulses and the at least one sequence of slave channel laser pulses are subjected to the orthogonal control. Preferably, the method of synthesizing optical waveforms is conducted with the optical parametric waveform synthesizer according to the above first general aspect of the invention.

Advantageously, the inventive orthogonal control of the optical parametric waveform synthesizer includes sensing all required parameters, in particular temporal and phase pulse properties of the master and slave channel laser pulses, and apply loop control, in particular feedback, e.g. proportional/integral, or feedforward, like predictive control, which is distributed to the different actuator devices in the optical parametric waveform synthesizer. Despite of a mutual interdependence of the parameters, the actuator device of each loop control is driven such that the other parameters are not influenced (orthogonal control). This allows for stabilization of one control variable by a control loop without degrading the control of the other control variables. This generally happened with the conventional techniques of controlling an optical parametric waveform synthesizer, wherein every actuator influenced more than one property directly or indirectly (e.g., cross-talk effects). On the contrary, the inventive method of deconvolution of the different processes is achieved by the orthogonalization of the control loops, preferably implemented by an orthogonalization algorithm and/or an orthogonalization circuit. In particular, contrary to [2], the inventors have found that suppressing fluctuations in relative phase and relative timing between slave channel and master channel, together with controlling the spectral intensity and CEP of the master channel results in a substantial stabilization of the optical parametric waveform synthesizer.

Contrary to [2], which just mentions one single BOC and one single delay line in the active stabilization system, the invention uses multiple detector devices, including e.g., a CEP sensor, a relative phase-difference sensor, a relative arrival time sensor as well as associated individually operating actuators which are specifically driven by the inventive matrix based control system. Furthermore, the BOC used in [2] has no phase sensitivity or CEP measuring capability.

Orthogonalization as mentioned in [5] and [7] is restricted to the control of linear actions in mode-locked lasers, e.g., by changing cavity dispersion by piezo swivel or repetition rate due to piezo length change. It is one of the important and unexpected results obtained by the inventors that orthogonal control needs to be used to stabilize and control a parametric waveform synthesizer, wherein the orthogonal control acts on actuator devices influencing strongly nonlinear (exponential) parametric gain in the optical parametric amplifier units.

As further advantages, the invention provides a stable and flexible control system with single-shot (single pulse) capabilities and online analysis of the system behavior. Adjusting the spectral intensity of the optical waveforms can be facilitated by a control of the seed source device and the optical parametric amplifier device. Furthermore, the number of control loops can be kept low without compromising the degrees of freedom for synthesis or the stability of the synthesized waveform, as the inherent properties of OP(CP)A-based parallel synthesizers are exploited.

As a further important advantage, the optical parametric waveform synthesizer can be implemented with any type of optical amplifier device. The term "optical amplifier device" refers to an amplifier setup, generally comprising at least two amplification channels (or: amplification lines), indicated as master channel and at least one slave channel, which are configured for optical parametric amplification of laser pulses, including OPA, OPCPA, DC-OPA, NOPA, DOPA, FOPA etc., derived from the pump pulses and the master and slave seed or amplified seed pulses. The pump source device is adapted for creating at least one sequence of pump pulses. In particular, the pump source device may comprise a single pump source creating one sequence of pump pulses for pumping all amplification channels. Alternatively, the pump source device may comprise multiple pump sources creating different pump pulses with different pulse parameters for specifically pumping the amplification channels.

The repetition frequencies of the at least one sequence of pump pulses, the sequence of master seed pulses and the at least one sequence of slave seed pulses can be identical (e.g., both at 1 kHz) or different. With different repetition frequencies, the pump sequences preferably have a lower repetition frequency compared with the seed pulses (e.g., seed at 1 kHz, but pump at 10 Hz).

Each channel has at least one optical parametric amplifier unit. A single stage amplification is possible, but two or more amplification stages are preferred in terms of increasing the signal-to-noise-ratio of the amplified pulses and output energy in each channel. More than two amplification channels are preferred for increasing the bandwidth of the synthesized optical waveforms to be obtained. The master channel is controlled such that the laser pulses are identical from shot-to-shot with respect to their spectral content and spectral phase/CEP. The master channel provides a reference channel for the at least one slave channel. The slave channel(s) is/are the remaining amplification channel(s), which is/are controlled for adjusting the temporal position and phase of the slave channels laser pulses relative to the master channels laser pulses.

According to a preferred embodiment of the invention, the detector devices are arranged for sensing the pulse temporal and phase properties, including the CEP of the master and slave seed pulses, preferably sensed by at least one CEP sensor, a relative phase between the master channel laser pulses and the slave channel laser pulses at the beam combiner device, preferably sensed by at least one phase difference sensor, and a relative arrival time between the master channel laser pulses and the slave channel laser pulses at the beam combiner device, preferably sensed by at least one first relative arrival time sensor. Accordingly, the control system is configured for simultaneously creating control signals for controlling at least the CEPs of the master and slave seed pulses, a temporal relationship between the master channel laser pulses and the slave channel laser pulses, preferably via acting on slave delay lines in the beam path of the pump pulses in the at least one optical parametric amplifier unit of the at least one slave channel, and a relative phase relationship between the master channel laser pulses and the slave channel laser pulses), preferably via acting on slave delay lines in the beam path of the seed pulses in the at least one optical parametric amplifier unit of the at least one slave channel.

With the conventional techniques (e.g., [4]), it was considered to be enough to stabilize the relative temporal relationship of the master channel laser pulses and the slave channel laser pulses, using an optical balanced cross-correlator (or similar technique) which feeds back to a delay stage to stabilize the output. On the contrary, the invention uses control loops on the relative phase and on the relative temporal relationships between the outputs of the master and slave channels, wherein in particular these control loops are orthogonalized. Advantageously, this results in an improved stabilization of the optical parametric waveform synthesizer in terms of both carrier wave phase and relative timing. Advantageously, the invention considers all important degrees of freedom and actively stabilizes them by the control system.

Optionally, the control system can be additionally configured for creating control signals for controlling a relative temporal relationship between the pump pulses and the master seed pulses in the at least one optical parametric amplifier unit of the master spectral channel, simultaneously with the above other control signals. However, this additional control loop can be omitted if the master channel is sufficiently stable or stabilized with a separate master channel control device (see below).

Preferably, the CEP sensor comprises an Nf-Mf beating sensor (n and m: unequal non-negative integers) being arranged for sensing beating signals of spectral components between at least one of the master and slave seed pulses. Depending on the configuration of the seed source device, optionally with multiple seed channels, multiple Nf-Mf beating sensors can be provided, each being configured for sensing CEP in one of the seed channels. Particularly preferred, an f-2f beating sensor is used. The beating sensor has particular advantages for precise and immediate CEP measurements.

With a further preferred variant of the invention, the at least one phase difference sensor comprises an f-Nf spectral domain beating sensor, with N=0, 1, 2, . . . , being arranged for sensing beating signals of spectral components between the master channel laser pulses and the slave channel laser pulses of the at least one slave channel. If multiple slave channels are provided, multiple phase difference sensors are used each being assigned to the master channel and one of the slave channels. Particularly preferred, an f-f spectral domain beating sensor is used if there are spectral components overlapping between the channels. For the other cases, an f-2f spectral domain beating sensor is preferred. The spectral domain beating sensor also has particular advantages for precise and immediate phase measurements.

With yet a further preferred variant of the invention, the at least one first relative arrival time sensor comprises a correlation sensor being arranged for measuring the arrival time difference between the master channel laser pulses and the slave channel laser pulses. If multiple slave channels are provided, multiple first relative arrival time sensors are used each being assigned to the master channel and one of the slave channels. Preferably the first relative arrival time sensor is a laser pulse detector device as disclosed in the specification of European patent application No. 16001475.9, being published after the priority date of the present specification. With regard to the structure and operation of the laser pulse detector device, the disclosure of the European patent application No. 16001475.9 is incorporated to the present specification by reference.

Generally, the term "control system" refers to an electronic circuitry being arranged for receiving output signals from the detector devices, creating control signals and supplying the control signals to actuator devices included in the seed source device and the optical parametric amplifier device. The control signals are created in dependency on set-points being preselected for creating a specific optical waveform to be obtained. The electronic circuitry is adapted for creating the control signals by an orthogonalization of the control loops included in the control system. With preferred examples, the electronic circuitry may comprise a computer circuitry being configured for running a software implementing the orthogonalization and/or a hardware electronic device implementing the orthogonalization. The control system can be adapted for conducting a feedback control or a feedforward control.

Furthermore, the control system can be used not only for stabilizing the optical waveforms, in particular from pulse to pulse, but also for setting a desired pulse shape of the optical waveforms. To this end, a control system user interface can be connected with the control system, wherein the control system user interface is arranged to provide the set point parameters to the control system and the control parameters of the orthogonalized control.

According to a particularly preferred embodiment of the invention, the control system includes an orthogonalized control matrix (or: active stabilization matrix), preferably a feedback matrix, being arranged for creating the control signals. The control matrix is an arrangement of control elements (or: stabilization elements), each of which receiving an input and the corresponding set point parameter from one of the detector devices connected with the control matrix and calculating a correction signal for controlling one of the actuator devices connected with the control matrix. Accordingly, with m detector devices and n actuator devices, the control matrix includes m*n control elements. The specific control signal delivered by the control matrix to each of the actuator devices is a superposition, in particular a linear combination, of the calculated correction signals of the control elements associated to the respective actuator device. The characteristic control function of the control elements, in particular PID-control and coupling factor of the control elements, is obtained by experimental tuning procedures (experimental calibration of the control matrix) or by numerical simulations (numerical calibration of the control matrix).

With a preferred example, the orthogonalized control matrix is implemented with a Field Programmable Gate Array (FPGA). As the observables for absolute CEP of the seed and/or the individual channel outputs, the envelope timing and relative phase between channel outputs are interconnected with each other, all acquired detector data are collected and applied to the control matrix, being configured for stabilizing every observed drift away from the set-point to every actuator device in an orthogonalized feedback control scheme. This in particular includes a CEP-changing actuator for the seed (or for the driver of multiple seeds), an arrival time synchronization for the different spectral channels of the synthesizer acting on the last-stage pump path and a phase synchronization for the different channels acting on seed or amplified seed paths before the last stage OP(CP)A unit.

According to a further preferred embodiment of the invention, each of the master channel and/or the at least one slave channel includes multiple optical parametric amplifier units, in particular OPA stages, e.g., OPA crystals. Preferably, the control system is configured for controlling the temporal relationship between the master channel laser pulses and the slave channel laser pulses, via acting on the slave delay lines in the beam path of the pump pulses in a last optical parametric amplifier unit of the at least one slave channel. While the first stages may provide a high gain of around 10000 and the last stage maybe a factor of 10, the last one puts the main energy in the pulse. This is why controlling the last OPA to manipulate timing and phase of the output with respect to the other outputs is preferred. Furthermore, the control system is arranged for controlling the phase relationship between the master channel laser pulses and the slave channel laser pulses, via acting on the slave delay lines in the beam path of the seed pulses in the last optical parametric amplifier unit of the at least one slave channel.

According to a further particularly preferred embodiment of the invention, the master channel is stabilized independently of the at least one slave channel and the seed source device. A master channel control device is provided additionally to the control system, wherein the master channel control device is adapted for stabilizing the spectral intensity characteristics and the CE-phase of the master channel laser pulses. Advantageously, the master channel laser pulses are always identical from shot to shot, thus providing an absolute reference for the slave channel laser pulses.

Advantageously, the master channel control device eliminates drifts of the spectrum and/or the CEP of the master channel laser pulses. To this end, the detector devices preferably include a spectrometer device for sensing the spectral intensity characteristics of amplified master seed pulses at an output of one of multiple optical parametric amplifier units of the master channel and a second relative arrival time sensor for sensing a relative arrival time of the amplified master seed pulses and the pump pulses at the last optical parametric amplifier unit of the master channel. Output signals of the spectrometer device and the second relative arrival time sensor are received by the master channel control device, which creates and supplies control signals to actuator devices in the master channel.

As a further advantage of the invention, multiple variants of providing the seed source device are available. Preferably, the seed source device comprises a combination of one single white-light pulse source for creating a sequence of broadband pulses and a beam separator device for separating the sequence of broadband pulses to the sequences of master and slave seed pulses, preferably with different spectral intensity content. With this embodiment of the invention, the detector devices advantageously comprise one single CEP sensor only which is arranged for sensing the CEP of the pulse source driving the single white-light pulse source, and the control system is configured for adjusting and stabilizing the CEP of the broadband pulses. Alternatively, the seed source device may comprise multiple, e.g., 2 or more, single white-light pulse sources. Again, one single CEP sensor can be used which is arranged for sensing a CEP of a pulse source driving the multiple single white-light pulse sources.

According to a further particularly preferred embodiment of the invention, the seed source device is arranged for creating multiple, e.g., 2 or more, sequences of slave seed pulses. Accordingly, the optical parametric amplifier device includes multiple slave channels each with at least one optical parametric amplifier unit for creating a sequence of slave channel laser pulses by non-linear optical interactions using the pump pulses and one of the sequences of slave seed pulses. Advantageously, the provision of 2 or more sequences of slave seed pulses introduces additional degrees of freedom for adjusting the spectral intensity of the optical waveforms to be obtained.

BRIEF DESCRIPTION OF THE DRAWINGS

Further advantages and details of the preferred embodiments of the invention are described in the following with reference to the attached drawings, which show in.

DETAILED DESCRIPTION OF PREFERRED EMBODIMENTS

Advantageous features of preferred embodiments of the invention are described in the following with exemplary reference to an optical parametric waveform synthesizer with an optical parametric amplifier device being configured with one master channel and two slave channels. It is emphasized that the invention is not restricted to this embodiment. Alternatively, the invention can be implemented with one slave channel or more than two slave channels. Furthermore, exemplary reference is made to an optical parametric waveform synthesizer with a pump source device creating one sequence of pump pulses for pumping all amplification channels. Alternatively, the invention can be implemented with a pump source device supplying different pump pulses with different pulse parameters to the different the amplification channels. Details of optical parametric (chirped-pulse) amplification, creating nonlinear effects, PID, feedforward, feedback or other active control schemes, or light detection with the detector devices are not described as far as they are known as such from conventional techniques.

Preferred Embodiment of the Optical Parametric Waveform Synthesizer

Figure 1:
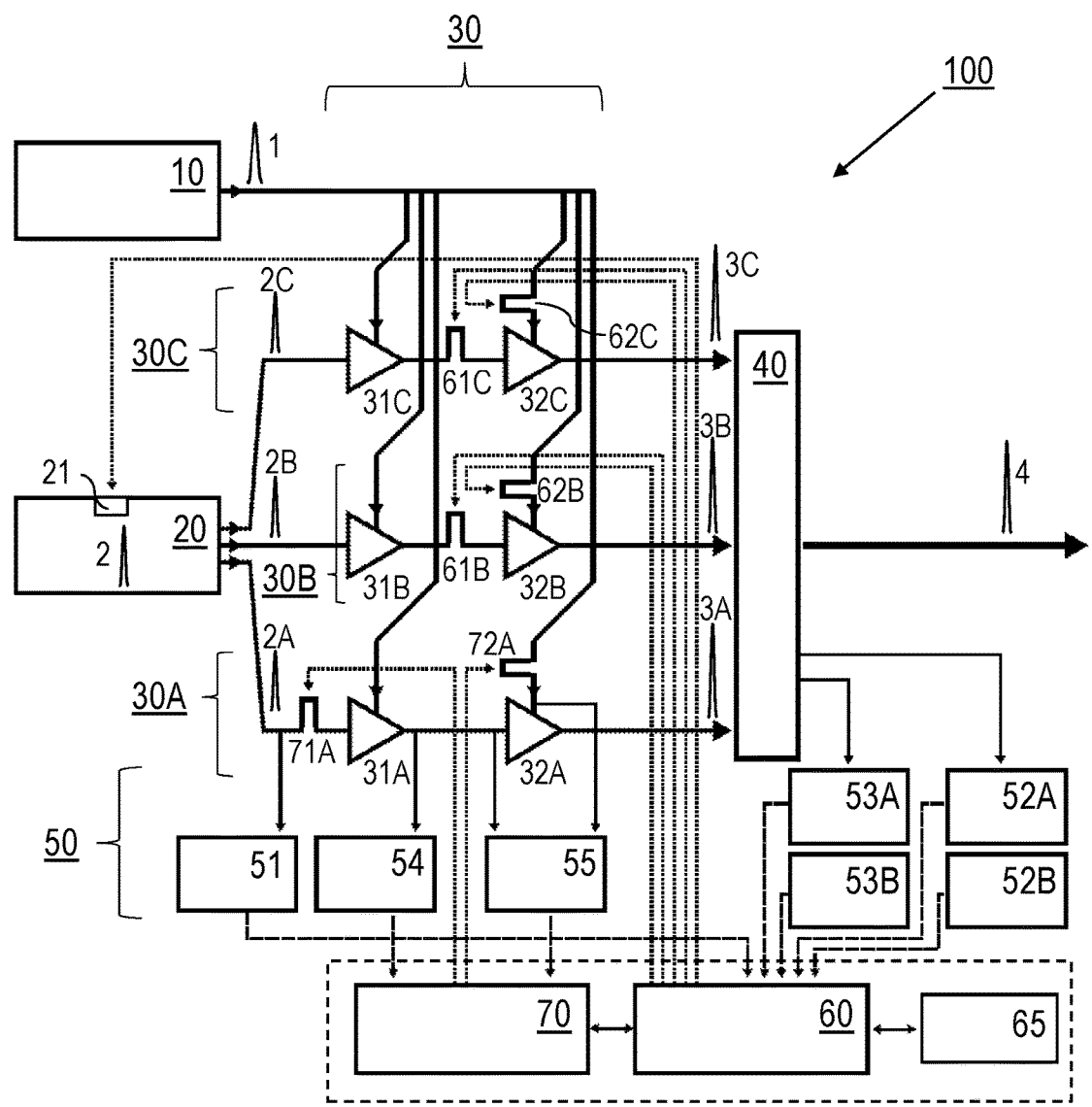
FIG. 1: a schematic illustration of an optical parametric waveform synthesizer according to a preferred embodiment of the invention.

FIG. 1 illustrates an embodiment of the optical parametric waveform synthesizer 100, including a pump source device 10, a seed source device 20, an optical parametric amplifier device 30 with a master channel 30A and two slave channels 30B, 30C, a beam combiner device 40, detector devices 50, a control system 60 and a master channel control device 70. FIG. 1 is a schematic drawing, wherein details of optical components, like deflection mirrors, focusing lenses, dispersion managing optical components etc., or mechanical components, like piezoelectric drivers are not shown. In practice, these components are provided as it is known from conventional optical setups, in particular from optical parametric waveform synthesizers and/or optical parametric amplifiers.

The pump source device 10 comprises a pump laser, e.g., a pulsed solid state laser, like a Ti:Sapphire-, Yb:YAG-, Yb:YLF-, Nd:YAG-laser creating pump pulses 1, e.g., with a repetition rate of 1 kHz, a duration of 150 fs, a centre wavelength of 800 nm, a pulse energy of 20 mJ and an average power of 20 W.

The seed source device 20 includes a CEP stable laser source, like a passive-CEP-stabilized OPA, e.g., driven by a Ti:Sapphire laser, creating fs laser pulses 2, e.g., with a repetition rate of 1 kHz, a duration of 100 to 150 fs, a centre wavelength of 1 µm, and a pulse energy of some µJ. Furthermore, the seed source device 20 includes beam splitters, splitting the initial fs laser pulses 2 to three sequences of fs laser pulses, which drive three white-light generation crystals, resulting in one sequence of master seed pulses 2A and two sequences of slave seed pulses 2B, 2C. The centre wavelengths and the white-light generation crystals, e.g., sapphire, YAG, $CaF_2$ crystals, are selected such that master seed pulses 2A and the slave seed pulses 2B, 2C have a centre wavelength of 600 nm, 800 nm, and 1.5 µm, correspondingly and a duration of 150 fs. Instead of whitelights a hollow-core fiber compressor can be used to broaden the spectra of the seed source driving laser. Due to preservation of phase stability in the white-light generation process, the master and slave seed pulses 2A, 2B, 2C have fixed CEP-relation between each other.

The seed source device 20 includes an actuator device 21 for adjusting the CEP of the master and slave seed pulses 2A, 2B, 2C. The actuator device comprises e.g., a dispersion setting device, like a pair of movable glass wedges being arranged for adjusting the dispersion in the laser source. Alternatively, the actuator device may comprise three components each being arranged for acting on the CEP of one of the master and slave seed pulses 2A, 2B, 2C. As a further alternative, if the seed source device uses an OPA for passive-CEP-stabilization from a seed source device driving laser with varying CEP, the actuator device may comprise a delay line for adjusting the pump beam path length at the OPA for the generation of the passive-CEP-stabilized driving laser which can be spectral broadened by white-light generation to provide the desired master/slave seeds 2A, 2B, 2C.

In the optical parametric amplifier device 30, the master channel 30A includes a series of one, two (as shown) or more optical parametric amplifier units (OPA stages) 31A, 32A, each including an optically non-linear crystal, like BBO, LBO, BiBo, KTP, KTA, ZGP, PPLN, PPKTP, or PPKTA, providing an amplification factor of e.g., 10 to 10000. The master seed pulses 2A are supplied via a first master delay line 71A as a seed to the first one of the optical parametric amplifier units 31A, and a portion of the pump pulses 1 is supplied to the optical parametric amplifier unit 31A for amplifying the master seed pulses 2A. The amplified output of the first optical parametric amplifier unit 31A is supplied as a seed to the subsequent optical parametric amplifier unit 32A, where a further amplification is obtained using another portion of the pump pulses 1 supplied via a second master delay line 72A, resulting in amplified master channel laser pulses 3A having a pulse energy of e.g., 150 µJ. Alternatively, with a three stage amplification, a pulse energy e.g., around 1.7 mJ can be reached.

The first and second master delay lines 71A, 72A are connected with the master channel control device 70, and they provide actuator devices for adjusting the temporal relationship between seed and pump pulses at the optical parametric amplifier units 31A, 32A and for stabilizing the spectral intensity and CEP of the master laser pulses 3A.

Each of the two slave channels 30B, 30C includes a series of at least two (as shown) or more optical parametric amplifier units (OPA stages) 31B, 32B, 31C, 32C, each including an optically non-linear crystal, like BBO, providing an amplification factor like in the master channel, e.g., 100. As a further example, with a three stage setup, the amplification factors are at the 1st stage 10000, at the 2nd stage 100, and at the 3rd stage 10. The optical parametric amplifier units 31B, 32B, 31C, 32C are arranged for amplifying the two sequences of slave seed pulses 2B, 2C and creating sequences of slave channel laser pulses 3B, 3C, having a pulse energy of e.g., 200 µJ.

Deviating from the master channel 30A, each of the slave channels 30B, 30C includes first and second slave delay lines 61B, 62B, 61C, 62C at the last one of the optical parametric amplifier units 32B, 32C. The first and second slave delay lines 61B, 62B, 61C, 62C are actuator devices being connected with the control system 60, which provides control signals to the actuator devices for adjusting the temporal relationship between seed and pump pulses at the optical parametric amplifier units 32B, 32C and for controlling and stabilizing the temporal and phase relationships of the master and slave channel laser pulses 3A, 3B and 3C. The slave delay lines 62B, 62C are arranged for controlling the relative temporal relationship between the master and the slave channel laser pulses 3A, 3B and 3C, and slave delay lines 61B, 61C are arranged for controlling the relative phase relationship between the master and the slave channel laser pulses 3A, 3B and 3C.

The master and slave channel laser pulses 3A, 3B and 3C have different spectral intensities, e.g., with centre wavelengths at 600 nm, 800 nm and 1.5 µm. The different spectral intensities are obtained by adjusting the phase-matching conditions at the optical parametric amplifier units of the master and slave channels. The beam combiner device 40 comprises an arrangement of dichroic beam splitters, like dichroic mirrors, gratings or prisms, being arranged for superimposing the master and slave channel laser pulses 3A, 3B and 3C onto a common beam path, thus synthesizing the optical waveforms 4 to be obtained. Additionally, beam portions on an output side of the beam combiner device 40 represent portions of the master and slave channel laser pulses 3A, 3B and 3C, which can be sensed with detector devices 52A, 52B, 53A, 53B as outlined in the following.

The detector devices 50 comprise a first group of detectors 51, 52A, 52B, 53A, 53B being connected with the control system 60 and second group of detectors 54, 55 being connected with the master channel control device 70.

The first group of detectors includes a CEP sensor 51, which senses the CEP of the master seed pulses 2A. Due to the common source, the CEP-behavior of the slave seed pulses 2B, 2C is sensed as well. The CEP sensor 51 is an f-2f beating sensor (f-2f spectral fringe sensor) superimposing spectral components of the master seed pulses 2A and detecting beating signals between the spectral components. The output signal of the CEP sensor 51 is delivered to the control system 60.

The first group of detectors further includes two phase difference sensors 52A, 52B sensing relative phases of the master channel laser pulses 3A relative to the slave channel laser pulses 3B, 3C of each slave channel 30B, 30C, resp. The phase difference sensors 52A, 52B comprise f-f spectral domain beating sensors sensing beating signals of spectral components of the master channel laser pulses 3A and the slave channel laser pulses 3B, 3C. The output signals of the phase difference sensors 52A, 52B are delivered to the control system 60.

Furthermore, the first group of detectors includes two first relative arrival time sensors 53A, 53B, each comprising a correlation sensor for measuring the arrival time difference between the master channel laser pulses 3A relative to the slave channel laser pulses 3B, 3C of each slave channel 30B, 30C, resp. Again, the output signals of the first relative arrival time sensors 53A, 53B are delivered to the control system 60.

The control system 60 includes an FPGA circuit being configured for implementing an orthogonal feedback matrix, the output signals of which driving the actuator device 21 and the first and second slave delay lines 61B, 62B, 61C, 62C.

The second group of detectors includes a spectrometer device 54, e.g., a grating spectrometer, for sensing the spectral properties of amplified master seed pulses at an output of the first optical parametric amplifier unit 31A of the master channel 30A, and a second relative arrival time sensor 55, e.g., a correlation sensor, for sensing a relative arrival time of the amplified master seed pulses and the pump pulses at the last optical parametric amplifier unit 32A of the master channel 30A. The spectral properties of the amplified seed pulse before the last optical parametric amplifier unit can be stabilized and controlled by the master channel control device 70 by varying the length of the beam path of the seed before the first optical parametric amplifier unit due to its chirp e.g. originating from the white-light generation process.

The master channel control device 70 includes control loops for stabilizing the CEP, temporal behavior and spectral content of the master channel laser pulses 3A in dependency on the output signals of the detectors 54, 55. Optionally, the master channel control device 70 can be connected with the control system 60 for adjusting the master channel laser pulses 3A in dependency on the current orthogonal control of the CEP, the slave channels and the waveform set-point.

The control system 60 and the master channel device 70 can be implemented as separate circuitries or with a common circuitry (see dashed box). Additionally, a control system user interface 65 can be provided, e.g., for selecting predetermined pulse properties of the optical waveforms to be obtained.

In practical operation, a sequence of the pump pulses 1 is created with the pump source device 10 and sequences of master and slave seed pulses 2A, 2B, 2C are created with the seed source device 20. The pump and seed pulses preferably have a rough synchronization, e.g., due to creation with the same source, injection seeding, or electronics synchronization). Depending on the CEP detected with the CEP sensor 51, the control system 60 controls the CEP of the master and slave seed pulses 2A, 2B, 2C. In the first OPA stages 31A, 31B, 31C the relative temporal drift (smaller than one percent of the pump pulse duration, e.g., about 2 fs) is negligible so that an arrival time control of the pump and seed pulses is not necessary at these stages. In the last OPA stages 32A, 32B, 32C, the arrival times of the amplified seed pulses from the preceding OPA stages 31A, 31B, 31C and the pump pulses are controlled by the control system 60 such that amplified master and slave channel pulses 3A, 3B and 3C are coherently combined with a fixed phase relationship at the beam combiner device. Due to the orthogonal control, driving the actuator devices in the seed source device 20 or one of the amplification channels does not influence the pulses in the other channels of the optical parametric amplifier device 30.

Design of the Control Matrix

Figure 2:
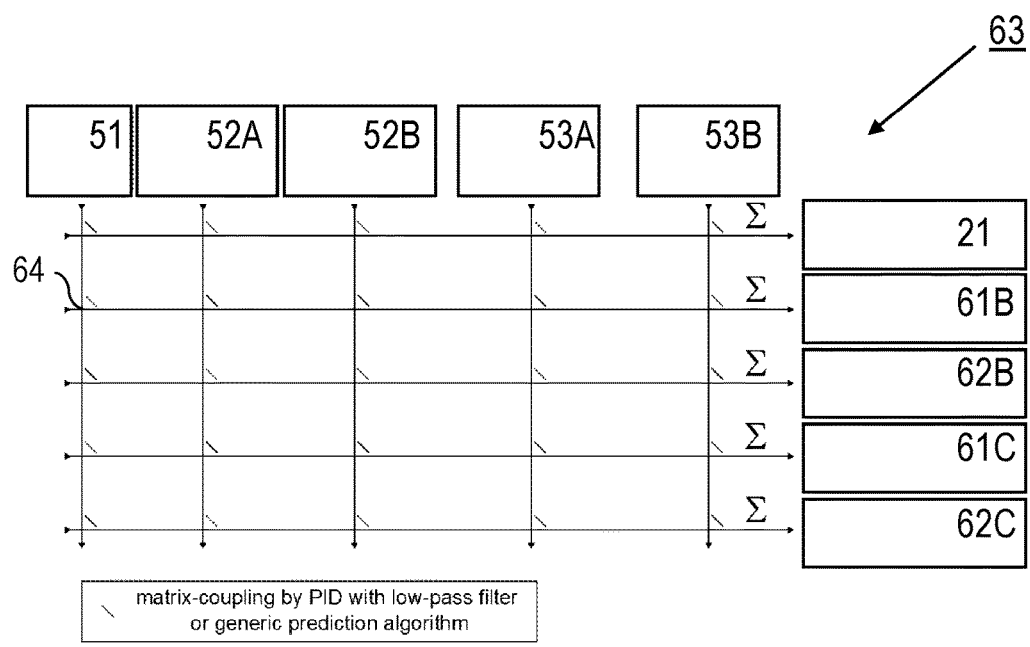
FIG. 2: a schematic illustration of a control matrix used according to a preferred embodiment of the invention.

FIG. 2 schematically illustrates the control matrix 63 implemented by the control system 60 of FIG. 1 with an arrangement of control elements 64. Each vertical line represents the measured error value (detector output) of one of the detectors 51, 52A, 52B, 53A, 53B. Each of the intersections represents a control element 64, like a PID or any other feedback or feedforward algorithm unit, calculating a correction signal depending on the measured error value and the set point value. All the calculated correction signals are collected along the horizontal lines and summed before they being applied to one of the actuator devices 21, 61B, 62B, 61C, 62C. This basically means, that every error signal can act on any actuator device with an individually defined set of control loop parameters.

The control matrix 63 is characterized by input signals (measured error values, detector output) x(i,t) with i positive integer numbers, i∈[1:m], with m=number of system input signals and the time t which is discretized in time-steps with $\Delta t = 1/f_{rep}$ where $f_{rep}$ is the repetition rate of the synthesized pulses, and output signals y(j,t) with j positive integer numbers, j∈[1:n] where n=number of actuator devices which affect the system e.g. seed delay lines before last amplifiers or pump delay lines in last stage amplifiers.

The input signals of the control matrix 63 come from at least one of the following sources:

1. Detectors 53A, 53B: difference of the intensity signals of two photo detectors PD1, PD2 from the balanced optical cross-correlator (BOC):

$$x_{BOC}(t) = I_{PD1}(t) - k \cdot I_{PD2}(t)$$

with a scaling factor of k to equalize slight imbalance of the two intensities.

2. Detector 52A, 52B: the unwrapped phase φ of one or more frequency components of a Fourier transform on the dataset of a 1-dimensional photo array detector (I(x,t)) which is placed in the Fourier plane of an optical spectrometer configuration (detecting the phase of spectral fringes):

$$I(f, t) = \mathcal{FT}(I(x, t))$$

$$\phi(t) = \arctan\left(\frac{\text{Im}(I(f_{fringes}, t))}{\text{Re}(I(f_{fringes}, t))}\right)$$

or calculated over several unwrapped phases which allow to retrieve the phase of spectral fringes.

3. Detector 51: Similar to 2., the optical input has an Mf-Nf beating with M unequal N. Each process multiplies the CEP by M (or N) and the beating then is a M-N representation of the CEP. Usually one part of the spectrum (f) is broadened and subjected to beating with a frequency doubled version of it (2f). The only difference is that there is only one input beam (e.g. master seed pulses) and not two (e.g. master and one slave laser pulses).

4. Furthermore, other parameters can be used to feedback to the system. These parameters might be: spectral shape, spectral intensity, spatial mode structure, spatial fringes and light intensity at any position inside the stabilized system.

Each input signal x(i,t) undergoes e.g., at least one of the following mathematical operations to yield a calculated active stabilization signal a(i,t):

(a) Filtering in time t with an arbitrary filter response function (the filter should be preferably a causal filter for low latency control): finite impulse response filter (FIR), moving average filter, or infinite impulse response filter (IIR); and/or (b) proportional-integral-differential controller (PID).

The processed input signals for every time step $t=t_0$ can be rewritten as a vector, where $t_0$ is the latest set of calculated control signals a(i,t):

$$a(i, t_0) = \vec{a}$$

This input vector is multiplied with a matrix of orthogonalization-factors B yielding ty(j)=$\vec{y}$:ol signals for each actuator j:

$$\vec{y} = B\vec{a}$$

This practically means, that every input observable x can act on every actuator y with a specific filter, PID-control and a coupling factor of $B_{ij}$, defined at the corresponding control element 64.

The following procedure exemplary describes one possible approach to retrieve the matrix values B for a given optical setup and feedback-implementation experimentally:

1. Set all control matrix values to zero $B=0_{mn}$;

2. Choose one measured error value and also a set point value (input signal) $x(i=i_0,t)$ to retrieve the necessary control signals (feedback values) for all actuators ($B_{i_0,j}$);

3. Inject a known disturbance to the actuator $y(j=j_0,t)$ mainly affecting the chosen observable, e.g. with a sinusoidal modulation:

$$y(j_0, t) = c(j_0) * \sin(\omega * t)$$

with $c(j_0)$ being the amplitude of the disturbance (e.g. displacement of an optical delay line, manipulated by a piezo driven stage) and ω the frequency of the sinusoidal modulation;

4. Start to inject the same sinusoidal modulation with another amplitude factor into another actuator:

$$y(j=j_1 \neq j_0, t) = c(j_1) * \sin(\omega * t)$$

5. Vary this factor until the effect on the observables $x(i \neq i_0, t)$ is minimized;
6. Repeat from step 4 for every actuator in the system $y(j,t)$ (n-times total);
7. The values $B_{i_0,j}$ are retrieved; and
8. Remove all disturbance injections, reset all prefactors to zero and repeat from step 2 until a set of prefactors for all observables $x(i)$ are retrieved (m-times total).

This procedure experimentally yields the values for the feedback matrix which describe a set of coupling strengths for every actuator to feedback to one observable without changing other observables. Advantageously, this procedure is true if the observables are coupled linearly with each other and even for small changes required to stabilize an optical system like the optical parametric waveform synthesizer. Alternatively, the experimental procedure can be replaced by a numerical simulation for obtaining the filter, PID-control and coupling factor of $B_{ij}$, defined at the control elements 64.

It is furthermore provided to set appropriate parameters for the filtering and the PID-control to close the feedback loop. This can be done with well-known procedures to allow fast setting time but no self-oscillation or excessive overshoot. The filters can be set according to only allow slow feedback (lowpass filter) or can be combined with other characteristics like a notch-filter to prevent excitation of an unwanted resonance inside the system (e.g. resonance of piezo-driven actuator).

The features of the invention disclosed in the above description, the drawings and the claims can be of significance both individually as well as in combination or sub-combination for the realisation of the invention in its various embodiments.

What is claimed is:

1. Optical parametric waveform synthesizer being configured for creating optical waveforms, comprising
    a pump source device being arranged for creating at least one sequence of pump pulses,
    a seed source device being arranged for creating a sequence of master seed pulses and at least one sequence of slave seed pulses,
    an optical parametric amplifier device having
        (a) a master channel with at least one optical parametric amplifier unit being arranged for creating a sequence of master channel laser pulses by non-linear optical interactions using one of the at least one sequence of pump pulses and the sequence of master seed pulses, and
        (b) at least one slave channel with at least one optical parametric amplifier unit being arranged for creating at least one sequence of slave channel laser pulses by non-linear optical interactions using one of the at least one sequence of pump pulses and the at least one sequence of slave seed pulses, wherein
    the master channel and the at least one slave channel are configured such that the sequence of master channel laser pulses and the at least one sequence of slave channel laser pulses have different spectral intensity characteristics,
    a beam combiner device being arranged for coherently combining the master channel laser pulses and the slave channel laser pulses, thus synthesizing the optical waveforms to be obtained,
    detector devices being arranged for sensing a relative arrival time between the master channel laser pulses and the slave channel laser pulses at the beam combiner device, and
    a control system being arranged for controlling a relative temporal relationship between the master channel laser pulses and the slave channel laser pulses on the basis of output signals of the detector devices, wherein
    the detector devices are arranged for further sensing pulse temporal and phase properties of the master and slave seed pulses and a relative phase between the master channel laser pulses and the slave channel laser pulses at the beam combiner device, and
    the control system is configured for controlling:
        a carrier-envelope-phase of the at least one of the master and slave seed pulses and the master channel laser pulses, and
        the relative temporal relationship and a relative phase relationship between the master channel laser pulses and the slave channel laser pulses,
    by an orthogonal control of the seed source device and the optical parametric amplifier device.

2. The optical parametric waveform synthesizer according to claim 1, wherein the detector devices comprise
    at least one carrier-envelope phase (CEP) sensor being arranged for sensing carrier-envelope phases (CEPs) of the master and slave seed pulses,
    at least one phase difference sensor each being arranged for sensing the relative phase between the master channel laser pulses and the slave channel laser pulses of the at least one slave channel at the beam combiner device, and
    at least one first relative arrival time sensor being arranged for sensing the relative arrival rime between the master channel laser pulses and the slave channel laser pulses of the at least one slave channel at the beam combiner device, and
    the control system is configured for simultaneously creating control signals controlling at least the following parameters
    CEPs of the master and slave seed pulses,
    a temporal relationship between the master channel laser pulses and the slave channel laser pulses, via acting on slave delay lines in a beam path of the pump pulses in the at least one optical parametric amplifier unit of the at least one slave channel, and
    a phase relationship between the master channel laser pulses and the slave channel laser pulses, via acting on slave delay lines in the beam path of seed pulses or amplified seed pulses in the at least one optical parametric amplifier unit of the at least one slave channel.

3. The optical parametric waveform synthesizer according to claim 2, wherein
    the at least one CEP sensor comprises an Nf-Mf beating sensor (N and M: unequal integers) being arranged for sensing beating signals between spectral components of at least one of the master and slave seed pulses,
    the at least one phase difference sensor comprises an f-Nf spectral domain beating sensor, with N=0, 1, 2, . . . , being arranged for sensing beating signals between spectral components of the master channel laser pulses and the slave channel laser pulses of the at least one slave channel, and
    the at least one first relative arrival time sensor comprises a correlation sensor being arranged for measuring an arrival time difference between the master channel laser pulses and the slave channel laser pulses.

4. The optical parametric waveform synthesizer according to claim 2, wherein
    the control system includes an orthogonalized control matrix being arranged for creating the control signals.

5. The optical parametric waveform synthesizer according to claim 2, wherein each of the at least one slave channel includes multiple optical parametric amplifier units and the control system is configured for controlling
- the temporal relationship between the master channel laser pulses and the slave channel laser pulses, via acting on the slave delay lines in the beam path of the pump pulses in a last optical parametric amplifier unit of the at least one slave channel, and
- the phase relationship between the master channel laser pulses and the slave channel laser pulses, via acting on the slave delay lines in the beam path of the seed pulses in the last optical parametric amplifier unit of the at least one slave channel.

6. The optical parametric waveform synthesizer according to claim 5, wherein the master channel includes
- a master channel control device being configured for stabilizing the spectral intensity characteristics and the CEP of the master channel laser pulses.

7. The optical parametric waveform synthesizer according to claim 6, wherein the detector devices comprise
- a spectrometer device being arranged for sensing a spectral intensity of amplified master seed pulses or amplified master channel laser pulses at an output of one of multiple optical parametric amplifier units of the master channel, and
- a second relative arrival time sensor being arranged for sensing a relative arrival time of amplified master seed pulses and the pump pulses at the last optical parametric amplifier unit of the master channel, wherein
- the master channel control device is configured for stabilizing the spectral intensity characteristics and the CEP of the master channel laser pulses on the basis of output signals of the spectrometer device and the second relative arrival time sensor.

8. The optical parametric waveform synthesizer according to claim 1, wherein
- the seed source device comprises one single white-light pulse source being arranged for creating a sequence of broadband pulses and a beam separator device being arranged for spectrally selectively separating the sequence of broadband pulses to the sequences of master and slave seed pulses,
- the detector devices comprise one single carrier-envelope phase (CEP) sensor being arranged for sensing a CEP of the broadband pulses, and
- the control system is configured for adjusting and stabilizing the CEP of the broadband pulses.

9. The optical parametric waveform synthesizer according to claim 1, wherein the control system has at least one of the features
- the control system is adapted for conducting a feedback control or a feedforward control, and
- the control system is adapted for changing set points of the parametric waveform synthesizer for generating a desired optical waveform.

10. The optical parametric waveform synthesizer according to claim 1, wherein
- the seed source device is arranged for creating multiple sequences of slave seed pulses,
- the optical parametric amplifier device includes multiple slave channels each with at least one optical parametric amplifier unit being arranged for creating a sequence of slave channel laser pulses by non-linear optical interactions using one of the at least one sequence of pump pulses and one of the sequences of slave seed pulses.

11. Method of synthesizing optical waveforms, comprising the steps of
- creating at least one sequence of pump pulses with a pump source device,
- creating a sequence of master seed pulses and at least one sequence of slave seed pulses with a seed source device,
- creating a sequence of master channel laser pulses by non-linear optical interactions using one of the at least one sequence of pump pulses and the master seed pulses in a master channel with at least one optical parametric amplifier unit and creating at least one sequence of slave channel laser pulses by non-linear optical interactions using one of the at least one sequence of pump pulses and the slave seed pulses in at least one slave channel with at least one optical parametric amplifier unit, wherein the sequence of master channel laser pulses and the at least one sequence of slave channel laser pulses have different spectral intensity characteristics,
- coherently combining the master channel laser pulses and the slave channel laser pulses with a beam combiner device, thus synthesizing the optical waveforms to be obtained,
- sensing a relative arrival time between the master channel laser pulses and the slave channel laser pulses at the beam combiner device, using detector devices, and
- controlling a relative temporal relationship between the master channel laser pulses and the slave channel laser pulses on the basis of output signals of the detector devices by an control system, wherein the method includes the further steps of
- sensing pulse temporal and phase properties of the master and slave seed pulses and a relative phase between the master channel laser pulses and the slave channel laser pulses at the beam combiner device, using the detector devices, and
- controlling:
  - a carrier-envelope-phase of at least one of the master and slave seed pulses and the master channel laser pulses, and
  - the relative temporal relationship and a relative phase relationship between the master channel laser pulses and the slave channel laser pulses, by an orthogonal control of the seed source device and the optical parametric amplifier device.

12. The method according to claim 11, wherein the detector devices comprise
- at least one carrier-envelope phase (CEP) sensor being arranged for sensing the carrier-envelope phases (CEPs) of the master and slave seed pulses,
- at least one phase difference sensor each being arranged for sensing the relative phase between the master channel laser pulses and the slave channel laser pulses of the at least one slave channel at the beam combiner device, and
- at least one first relative arrival time sensor being arranged for sensing the relative arrival time between the master channel laser pulses and the slave channel laser pulses of the at least one slave channel at the beam combiner device, and
- the control system simultaneously creates control signals controlling at least the following parameters
- the CEPs of the master and slave seed pulses,
- a temporal relationship between the master channel laser pulses and the slave channel laser pulses, via acting on slave delay lines in a beam path of the pump pulses in the at least one optical parametric amplifier unit of the at least one slave channel, and a phase relationship between the master channel laser pulses and the slave channel laser pulses, via acting on slave delay lines in the beam path of the seed pulses or amplified seed pulses in the at least one optical parametric amplifier unit of the at least one slave channel.

13. The method according to claim 12, wherein
the control system includes an orthogonalized control matrix being arranged for creating the control signals.

14. The method according to claim 12, wherein each of the master channel and the at least one slave channel includes multiple optical parametric amplifier units and the control system simultaneously controls the temporal relationship between the master channel laser pulses and the slave channel laser pulses, via acting on the slave delay lines in the beam path of the pump pulses in a last optical parametric amplifier unit of the at least one slave channel, and the phase relationship of the master channel laser pulses with the slave channel laser pulses, via acting on the slave delay lines in the beam path of the seed pulses in the last optical parametric amplifier unit of the at least one slave channel.

15. The method according to claim 12, further comprising the step of
stabilizing the spectral intensity characteristics and the CEP of the master channel laser pulses by a master channel control device.

16. The method according to claim 15, comprising the steps of sensing a spectral intensity of amplified master seed pulses at a last one of multiple optical parametric amplifier units of the master channel with a spectrometer device, and sensing a relative arrival time of amplified master seed pulses and the pump pulses at the last optical parametric amplifier unit of the master channel with a second relative arrival time sensor, wherein the master channel control device stabilizes the spectral intensity characteristics and the CEP of the master channel laser pulses on the basis of output signals of the spectrometer device and the second relative arrival time sensor.

17. The method according to claim 11, including at least one of the features the control system conducts a feedback control or a feed forward control, and the control system changes set points for generating a desired optical waveform.

18. The method according to claim 11, comprising the steps of creating multiple sequences of slave seed pulses with the seed source device, and creating multiple sequences of slave channel laser pulses by non-linear optical interactions using one of the at least one sequence of pump pulses and one of the sequences of slave seed pulses.

* * * * *